United States Patent
Molebny et al.

(10) Patent No.: US 6,409,345 B1
(45) Date of Patent: Jun. 25, 2002

(54) METHOD AND DEVICE FOR SYNCHRONOUS MAPPING OF THE TOTAL REFRACTION NON-HOMOGENEITY OF THE EYE AND ITS REFRACTIVE COMPONENTS

(75) Inventors: Vasyl V. Molebny, Kiev (UA); Ioannis Pallikaris, Heraklion Crete (GR); Youssef Wakil, Houston, TX (US); Sergiy Molebny, Kiev (UA)

(73) Assignee: Tracey Technologies, LLC, Houston, TX (US)

( * ) Notice: Subject to any disclaimer, the term of this patent is extended or adjusted under 35 U.S.C. 154(b) by 0 days.

(21) Appl. No.: 09/634,487

(22) Filed: Aug. 8, 2000

(51) Int. Cl.⁷ .................................................. A61B 3/10

(52) U.S. Cl. ..................................................... 351/212

(58) Field of Search ............................... 351/205, 206, 351/211, 212, 246, 159, 215, 160 H, 160 R, 161, 177; 606/4, 5

(56) References Cited

U.S. PATENT DOCUMENTS

| | | | |
|---|---|---|---|
| 3,290,927 A | 12/1966 | Gambs | 73/80 |
| 4,691,716 A | 9/1987 | Tanne | 128/774 |
| 4,796,989 A | 1/1989 | Fukuma et al. | 351/212 |
| 5,148,205 A | 9/1992 | Guilino et al. | 351/159 |
| 5,214,455 A | 5/1993 | Penney et al. | |
| 5,258,791 A | 11/1993 | Penney et al. | 351/211 |
| 5,293,871 A | 3/1994 | Reinstein et al. | 128/660.06 |
| 5,414,478 A | 5/1995 | Van Galderen | 351/212 |
| 5,418,714 A | 5/1995 | Sarver | 364/413.13 |
| 5,581,405 A | 12/1996 | Meyers et al. | 359/571 |
| 5,589,897 A | 12/1996 | Sinclair et al. | 351/223 |
| 5,722,427 A | 3/1998 | Wakil et al. | 128/898 |
| 5,841,511 A | 11/1998 | D'Souza et al. | 351/212 |
| 5,847,801 A | 12/1998 | Sarver et al. | 351/206 |
| 5,875,019 A | 2/1999 | Villani | 351/211 |
| 5,953,100 A | 9/1999 | Sarver et al. | 351/206 |
| 6,000,800 A | 12/1999 | Webb et al. | 351/211 |
| 6,082,856 A * | 4/2000 | Dunn et al. | 351/160 H |
| 6,234,631 B1 * | 5/2001 | Sarver et al. | 351/212 |

FOREIGN PATENT DOCUMENTS

JP                 609544               7/1979

OTHER PUBLICATIONS

Corneal Topography The State of the Art by James P. Gills, Donald R. Sanders, Spencer P. Thornton, Robert G. Martin, Johnny L. Gayton, Jack T. Holladay –Chapter % –The EyeSys 2000 Corneal Analysis System by Spencer P. Thornton, M.D. FACS and Josiph Wakil, M.D. MEE.

EyeSys 2000 Corneal Analysis System: The Ultimate in Corneal Topography from the Proven Leader ()Brochure). Copyright EyeSys Technologies, Inc., 1995.

EyeSys Vista: Hand–Held Corneal Topographer (Brochure).

(List continued on next page.)

*Primary Examiner*—George Manuel
(74) *Attorney, Agent, or Firm*—John W. Montgomery; Haynes and Boone, LLP

(57) ABSTRACT

An instrument for measuring aberration refraction of an eye is provided, having: a lens system defining an instrument optical axis and an alignment device for aligning the visual axis of the eye with the instrument optical axis. A light source produces a probing beam that is projected through the lens system parallel to the instrument optical axis and is selectably positionable partially off-set from the instrument optical axis for entering the eye parallel to the instrument optical axis at a plurality of locations on the cornea of the eye. A first photodetector measures the position of a first portion of the probing beam light scattered back from the retina of the eye to measure aberration refraction of the eye at a plurality of locations. A second photodetector synchronously measures the position of a second portion of the probing beam light reflected back from the cornea of the eye.

30 Claims, 10 Drawing Sheets

OTHER PUBLICATIONS

Ophthalmic Terninology: Speller and Vocabulary Builder –Third Edition –by Stein, Slatt, and Stein.

Contact Lenses: Update 1 –Chapter 4 –Corneal Topgraphy by J. James Rowsey and David J. Schanzlin (Copyright 1986 by Little, lBrouwn and Company).

Contact Lenses –Chapter 17 –Measurement of Corneal Curvature: Keratometer (Ophtalmometer) by Oliver H. Dabezies, Jr. and Jack T. Holladay (Copyright 1984 and Little, Brown and Company A Comprehensive Guide to Fitting Contact Lenses with EyeSys Pro–Fit Contact Lens Fitting Software by Beth A. Soper, C.O.A. (Eyesys System 2000 –Verson 3.1).

* cited by examiner

Figure 7
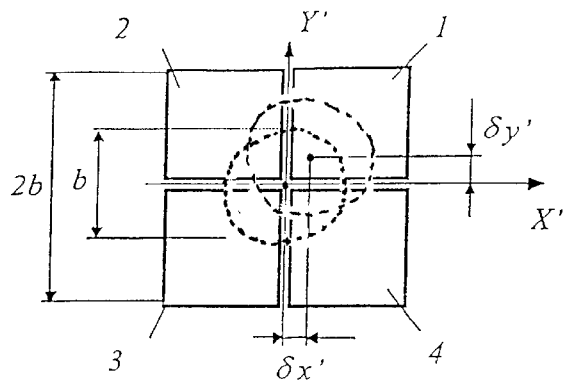
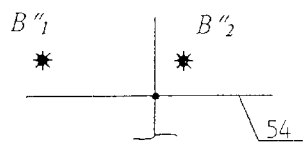
Figure 9
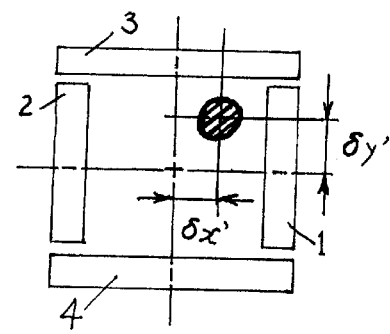
Figure 8
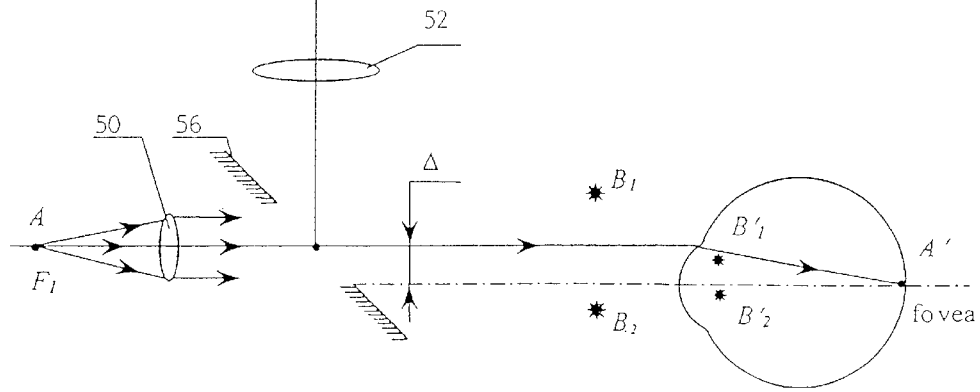

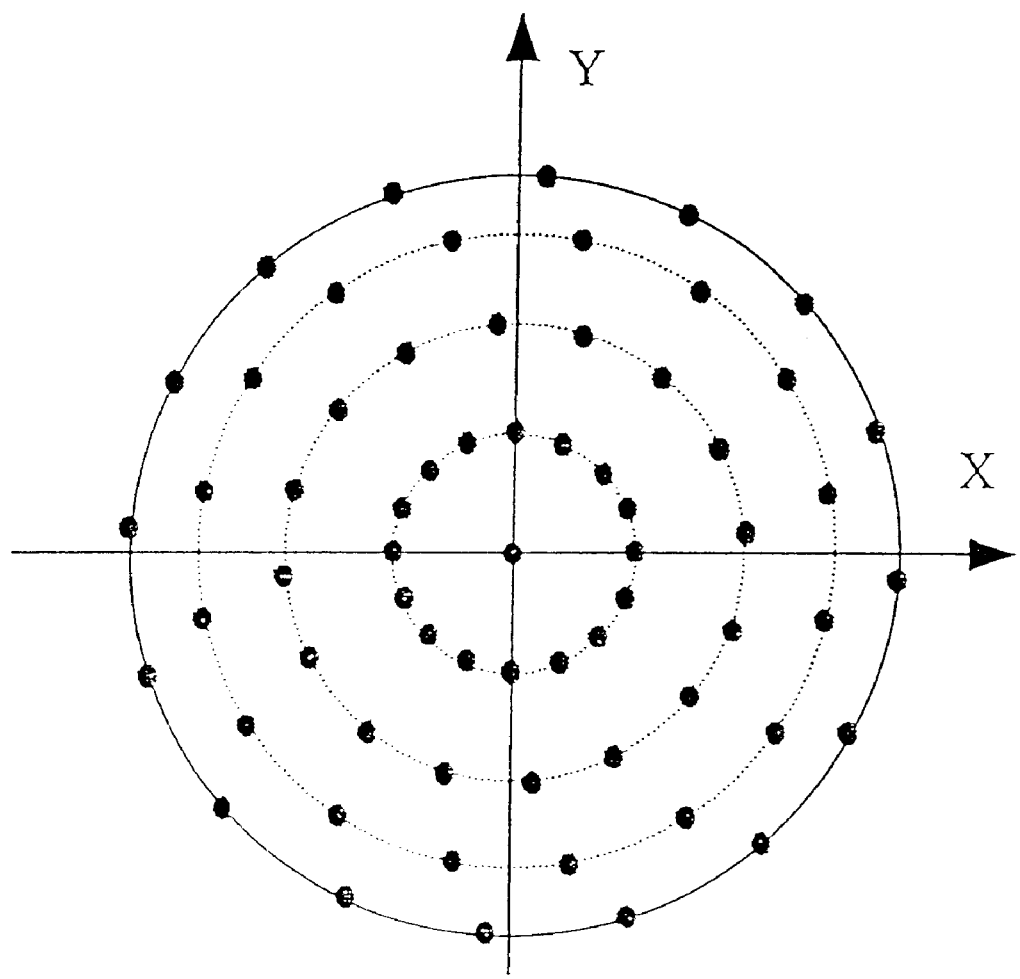
Figure *10*

METHOD AND DEVICE FOR SYNCHRONOUS MAPPING OF THE TOTAL REFRACTION NON-HOMOGENEITY OF THE EYE AND ITS REFRACTIVE COMPONENTS

CROSS-REFERENCE TO RELATED PATENTS AND APPLICATIONS

This is a continuation-in-part of PCT Application No. PCT/US99/23327 in which the US is a designated country and which claims Ukranian Patent Application No. 98105286 as a priority document.

TECHNICAL FIELD OF THE INVENTION

The present invention relates to medical ophthalmological equipment, more specifically, it relates to devices for measuring the refraction of the eye as a function of spatial pupil coordinates.

BACKGROUND OF THE INVENTION

A method and a device for mapping the total refraction non-homogeneity of an eye are set forth in prior co-pending PCT Application No. PCT/US99/23327 that includes directing into the eye a narrow laser beam, its axis being parallel to the visual axis of the eye under investigation, scanning the beam over the eye aperture, receiving a portion of light scattered by the retina, analyzing the position of the laser spot projected on the retina, and reconstructing from the data a map of the total refraction of the eye. A discussion of the details of the total refraction non-homogeneity determination have been incorporated herein and set forth below.

In many applications, information on the contribution of other refractive components of the eye may be helpful or necessary, as, for example, for subsequent corrective surgery.

For the purpose of measuring the surface shape of a cornea, a method is known of projecting a regular structure or regular patterns, such as a pattern of concentric disks onto the cornea, analyzing the reflected light and reconstructing from the analyzed data the shape and therefore the refraction distribution caused by the cornea. It has been discovered by Applicants that marrying the techniques for analyzing retina-scattered light and for analyzing cornea reflected light may give very useful information on the contribution to the total eye refraction of such other refractive components of the cornea, and/or the eye lens, that has not heretofore been successfully accomplished.

Measuring devices are known, for the study of the refraction component of the optical system of the eye, which depend on spatial pupil coordinates. These include M. S. Smirnov's device for measuring the wave aberration [1], Van den Brink's device for measuring the transverse aberration [2], N. M. Sergienko's device for measuring the physiological astigmatism [3], and a spatially resolved refractometer [4]. The above devices, based on Scheiner's principle, involve point-by-point investigation over utilizing a number of optical techniques. However, in using all such devices the direct participation of the patient is needed in the preliminary aligning of the eye and in the aberration measurements.

Major disadvantages of the above measuring devices are their low accuracy and productivity, a prolonged measurement process resulting in the patient's fatigue, variations in accommodation, and eye movements while taking measurements, thereby increasing the aberration measurement errors.

More advanced measuring devices are known, which do not require the patient to act as a link in the "measurement chain". These include a device for measuring the aberration by the Foucault's knife method [5], a device for measuring the wave aberration using Hartmann-Shack sensors [6–8], including measurements that incorporate adaptive optics completely compensating the wave aberration [9].

A common disadvantage of the measuring devices with a Hartmann-Shack sensor is the fixed field of view of the raster photoelectric analyzer of transverse aberrations due to the mechanically rigid construction of the lens raster and the invariable mutual spatial arrangement of the photosensitive elements of the charged coupled device or CCD camera. This results in a fixed configuration of grid sites at the pupil plane in which aberrations are measured, with no flexibility of reconfiguring these grid sites for more detailed measurements in separate zones of the pupil depending on their aberration properties.

Other disadvantages of existing devices include: they do not incorporate means for providing an accurate reproducible "linkage" of the patient's eye to the spatial co-ordinates of the measuring device; they do not incorporate a means for adjusting the accommodation of the patient's eye that is necessary for studying the dependence of aberrations on the accommodation characteristics; they are not capable of taking measurements on a dilated pupil without using medicines.

Refraction can also be measured using a spatially resolved objective autorefractometer as disclosed in U.S. Pat. No. 5,258,791 [10]. This device provides spatially resolved refraction data using a closed measuring loop which includes a reference pattern and a measurement beam. In this device, an origin of coordinates of the detector coincides with the center of the fovea image and the detector functions as a zero-position sensor.

The spatially resolved objective autorefractometer disclosed in U.S. Pat. No. 5,258,791 preferably using laser ray tracing, has a number of substantial problems relating to performance in the following basic and auxiliary functions: preliminary alignment of the optical axis of the device relative to the visual axis of the eye; accommodation monitoring of the patient's eye; allocation of points within the pupil at which refraction is measured; and measurement of the angle of laser beam incidence into the patients eye. Respective to the above basic and auxiliary functions, the above drawbacks are inherent to the device disclosed in U.S. Pat. No. 5,258,791.

Preliminary alignment of the optical axis of prior art devices relative to the visual axis of the eye may be problematic for at least the following reasons: first, the visual axis of the eye is assumed to be the line passing through the geometric center of the pupil and the fovea. However, it is known that the geometric center of the pupil does not always coincide with the visual axis due to the misalignment of the pupil opening and the optical axis of the cornea and the crystalline lens. In addition, the pupil may not be symmetrical.

Second, in prior art devices in which alignment is dependant on fixation of the patient's gaze at a focal point, changes in the position of the point at which the patients gaze is fixed results in angular movement of the patient's eye which disturbs the previous alignment. Consequently, both points (on the pupil and on the retina) through which the center line passes do not have a definite location.

Third, the focal points in devices without ametropia compensation can clearly be observed only with an emmetropic or normal eye. When the patient's eye is ametropic, such devices will see a diffused laser beam spot whose width increases with the ametropy. It is obvious that under such conditions the gaze cannot be fixed accurately in a certain direction, which is another factor preventing an accurate alignment. Another drawback of prior art refractometers is that the fovea and the photosensitive surface of the photodetector are optically coupled by the lenses only in the emmetropic or normal eye. In the event of an ametropic eye, the decentering or defocusing of the fovea image on the above-mentioned surface of the photoelectric detector causes additional refraction measurement errors which are not compensated for. The present invention is designed to compensate for this.

Fourth, a sufficiently bright laser radiation may irritate the fovea to such a degree that the eye begins to narrow its pupil reflexly. Therefore, before performance of the eye centering procedure, medicines paralyzing the ciliar body muscles are likely to be required, which changes the refractive properties of the eye as compared with its normal natural state.

The need for accommodation monitoring of the patient's eye has not been satisfied in prior art devices. As a consequence, the patient's eye can be accommodating at any distance. It is known that the refractive properties of the eye depend on the accommodation distance. Because the accommodation is unknown to the operator, it is impossible to correlate the refraction map and the eye accommodation.

It has become apparent to the present applicants that a spatially resolved refractometer should preferably include a device for adjusting to the patient's eye accommodation.

Prior art devices using electromechanical actuators greatly reduce the possibility of ensuring a high-speed scanning of the pupil and the possibility of shortening the duration of the ocular refraction measurement process.

In prior art devices using a disc or movable aperture bearing planar surface to control laser targeting, the aperture occupies only a small portion of the zone in which the laser beam intersects the planar surface. Thus, only that portion of the laser beam which is equal to the ratio of the area of one refraction measurement zone on the pupil to the entire pupil area passes through the aperture. Such a vignetting of the laser beam results in an uneconomical use of laser radiation and should be considered a major drawback of such designs.

Drawbacks in the measurement of the angle of laser beam incidence at which it crosses the necessary measurement zone of the pupil and the center of the fovea are inherent to designs which do not provide a sufficiently high refraction measurement speed. In such designs, the time of measuring the refraction at 10 measurement points of the pupil is up to one minute. During this period the patient's eye can move up to 100 times and change its angular position due to natural tremor, "jumps" and drift.

Systematic instrument errors have plagued prior aberration refractometers. Due to an irregular distribution of the light irradiance within the light spot on the retina, unequal photosensitivity across the surface photoelectric detector, time instability of the gain of preamplifiers connected to the photoelectric detector elements, and the presence of unsuppressed glares and background illumination the photodetector, the photodetector does not register a "zero" position of the spot on the fovea without systematic errors. Further, as a result of its own aberrations, the optical system providing for eye ray tracing contributes an angular aberration to the laser beam position. The present instrument incorporates structural elements which compensate for such errors and thus increase the refraction measurement accuracy.

What is needed is an improved electro-optical ray tracing aberration refractometer which makes it possible to achieve the following goals: flexibility of allocation of measuring points within the pupil and to pupil and improvement in the effectiveness of using lasers by reducing the vignetting of the laser beam at the aperture diaphragm; reduction in the duration of measuring refraction across the entire pupil to around 10–20 milliseconds; ensuring optical coupling of the photosensitive surface of the photodetector with the fovea even for ametropic eyes as well as for accommodation monitoring at any given distance; synchronously measuring both the total eye refraction aberrations and the component caused by cornea refraction characteristics maintaining incremental accuracy by interposing additional impingement points between impact points with wide variation in refraction characteristics; reduction in instrument errors when measuring aberration refraction; enhancement of the accuracy and definitiveness of instrument positioning relative to the patient's eye; the potential for automation of the positioning and controllability of the working distance between the patient's eye and the device components; and enablement of instrument positioning without medically dilating the pupil. The present invention provides the aforementioned solutions and innovations.

It has also been found that, due to noncoincidence of the points of primary information from the attempted combination of total eye refraction information and the surface shape of a cornea, and the followed approximation, any maps reconstructed from such cornea topography data and separately obtained total eye refraction aberration data would contain significant errors when reconstructing the differences. A workable device and method for synchronous mapping of the total refraction non-homogeneity of the eye and of the refraction components caused by the cornea would be desirable.

SUMMARY OF THE INVENTION

To avoid these and other drawbacks and solve the problems and produce a workable device and method for synchronous mapping of both the total refraction non-homogeneity of the eye and its refractive components, the following inventive technology has been devised. A device for synchronous measuring aberration refraction of an eye and calculation of the component of the total aberration refraction caused by the cornea has been accomplished with a device comprising a polarized light source producing a probing beam along a path to the eye. A beam shifter is provided to rapidly shift the probing beam to a plurality of spaced-apart, parallel paths for impacting the eye at a plurality of points on the cornea. Nonpolarized backscattered light from the retina of the eye is directed through a polarizing beam splitter onto a first position-sensitive detector by which the total eye refraction is determined for each of the plurality of impingement points. Synchronized with each impingement point determination of the total eye refraction, there is a polarized reflection from the impingement point on the cornea directed through the polarizing beam splitter and to a second position-sensitive detector for determining the refraction component caused by the cornea. A comparator can synchronously compare the total refraction for each impingement point to the component of refraction caused by the cornea and by subtraction can determine the component of refraction caused by the parts of the eye other than the cornea. This data can be placed in memory and/or can be supplied to a program device for map reconstruction and to a representative display of the refraction characteristics of the eye and its components.

For additionally improved resolution, a program device may be provided for inserting an additional measuring point or impingement point located between neighboring measuring points that produce a different value higher than a specified maximum difference threshold.

Thus, the object of the present invention is to provide an improved polarized light device for measuring the aberration refraction of the eye. The aberration refractometer allows estimates of the ametropy, astigmatism characteristics, simultaneously allows synchronous determination of component parts of total aberration refraction of the eye contributed by the cornea and therefore the components contributed by other portions of the eye and thereby allowing visual acuity and increased accuracy of calculations of the part of the cornea to be removed by photorefractive keratectomy [11] if necessary to correct eye refraction non-homogeneity or aberration.

In a preferred embodiment, the aberration refractometer comprises a light radiation source, preferably laser light or other polarized light; a telescopic system; a two-coordinate deflector consisting of two single-coordinate deflectors; a deflection angle control unit; an aperture stop; a field stop; a collimating lens; an interferential polarizing beam splitter; a first position-sensitive photodetector with an objective lens for detecting only the position of light backscattered from the retina; a second photosensitive photodetector with an objective for detecting only the position of polarized light reflected from the cornea; a comparator for point-by-point comparison of the retinal backscatter position and the cornea reflection position; and a data processing and display unit consisting of a computer, an analog-to-digital converter and a preamplifier. Use of laser or polarized light as a probing beam in combination with the interferential beam splitter allows the polarized light to be separated from the non-polarized light reflected back from the retina and prevents it being detected by the first photodetector and further allows polarized light reflected from the cornea to be detected by the second photodetector without detecting the backscattered light from the retina.

The instrument of the present invention is able to reduce the time needed for measuring the refraction, eliminate light beam energy losses at the aperture stop and create a flexible system for locating the measurement points on the pupil by providing the following: the telescopic system is positioned in the probing beam path after the two-coordinate first deflector at a distance corresponding to the coincidence of the entrance pupil of the telescopic system and the gap or zone between the single-coordinate deflectors, the aperture stop or diaphragm is placed between the lenses of the telescopic system at the point of coincidence of their foci, and the field stop or diaphragm is positioned in the plane of the exit pupil of the telescopic system and, at the same time, at the location of the front focus point of the collimating lens situated in front of the interferential polarizing beam splitter at such a distance from the patient's eye which is approximately equal to the focal distance of the collimating lens.

To ensure a constant optical coupling of the photosensitive surface of the first photodetector and the retina for both emmetropic and ametropic eyes, a group of lenses with variable optical power is installed between the interferential polarizing beam splitter and the eye, said group of lenses having the function to adjustably form the retina image of an ametropic eye at infinity regardless of the emmetropic or ametropic condition of the eye. The photosensitive surface of the first photodetector is conjugated with the front focal plane of the objective lens, being inserted following the interferential polarizing beam splitter on the path of the light scattered by the retina.

To provide for fixation of the patient's line of sight along the optical axis of the instrument and to compensate for accommodation of the eye at the required distance while keeping constant optical conjugation of the patient's eye with the photosensitive surface of the detector, a second beam splitter or an optical axis rotation mirror, as well as a plate with a gaze fixing test pattern or a test-target for sight fixation are optically coupled with the photosensitive surface of the photodetector and are located between the photodetector and the objective lens. A second optical group of lenses, with variable negative optical power and which function to form an image for the patient's eye of the test-target at a distance corresponding to the preset accommodation, is positioned between the second beam splitter or optical axis bending mirror and the interferential polarizing beam splitter. When an optical axis bending mirror is used, it is mounted on a movable base making it possible to displace the mirror so as to enable the light radiation scattered by the retina to reach the photodetector during the measurement of the patient's eye characteristics.

In one embodiment, to account for systematic refraction measurement errors, a second mirror, for bending or redirecting the optical axis of the probing laser beam is inserted in the laser beam path after the last optical element before entering the patient's eye. Following the second mirror, an optical calibration unit for simulating an eye is inserted. The optical calibration unit includes an axially movable or stationary retina simulator whose optical characteristics are equivalent to those of the human retina. The second optical axis bending mirror is installed on a movable base so that it can be moved into the probing laser beam path during measurement with the optical calibration unit and moved out when measuring the patients eye refraction.

To align the instrument relative to the patient's eye as well as to enhance accuracy and enable automation of the aligning process, the instrument is provided with a third beam splitter to insert a channel for eye alignment verification of the instrument and the patient's eye. In a preferred embodiment, the co-axial verification channel comprises one or more point of light sources and a TV or electro-optic detecting device, together serving to display the pupil and/or eye image and providing a permission channel to measure eye characteristics when the optical axis of the instrument and the visual axis of the patient's eye coincide. To enable the instrument to be used without dilating the pupil with a medicine, a laser radiation source and/or infrared light sources are incorporated into the coaxial verification alignment mechanism. It is contemplated that the instrument can be used to make refraction measurements under conditions simulating either day or night light conditions.

In an alternate embodiments it is further contemplated that the alignment verification can be done under the control of the operator of the device or can be automated. In one embodiment, the co-axial verification channel provides either visual or acoustic notification that coincidence between the instrument optical axis and the patient's visual axis is proximate or near to "on target" status. Once this status is attained, the instrument is "armed" electronically. Once full coincidence is attained, the measurement controller automatically causes spatially defined parallel light beams, preferably laser beams, to be rapidly fired and enter the eye through the input channel. Light reflecting from the retina is directed to the retinal spot detecting channel for spatial and intensity characterization. This process can permit upwards of at least 5 replicate measurements over 65 spatial locations to be taken within 15 milliseconds without the need for the patient to actively participate in the targeting and alignment process.

BRIEF DESCRIPTION OF THE DRAWINGS

For a more complete understanding of the present invention, including features and advantages, reference is now made to the detailed description of the invention along with the accompanying figures in which like numerals represent like elements and in which:

FIG. 7 is a schematic illustration of the operation of yet another embodiment of a device for measuring the total transverse aberration of a laser beam on the eye retina of both of a patient's eyes substantially simultaneously;

FIG. 8 is a schematic illustration of the operation of the lateral position sensing detector having a pair of X direction electrodes and a pair of Y direction electrodes;

FIG. 9 is a schematic illustration of the principle of operation of the means for positioning the measuring device in relation to the patient's eye;

FIG. 10 is an example of a map showing the location of ocular refraction measurement points, constructed with the aid of a computer;

DETAILED DESCRIPTION OF THE PREFERRED EMBODIMENTS

While the making and using of various embodiments and methods of the present invention are discussed in detail below, it should be appreciated that the present invention provides many applicable inventive concepts which may be employed in a variety of specific contexts. The specific embodiments discussed herein are merely illustrative of specific ways to make and use the invention and do not delimit the scope of the invention.

Figure 1:
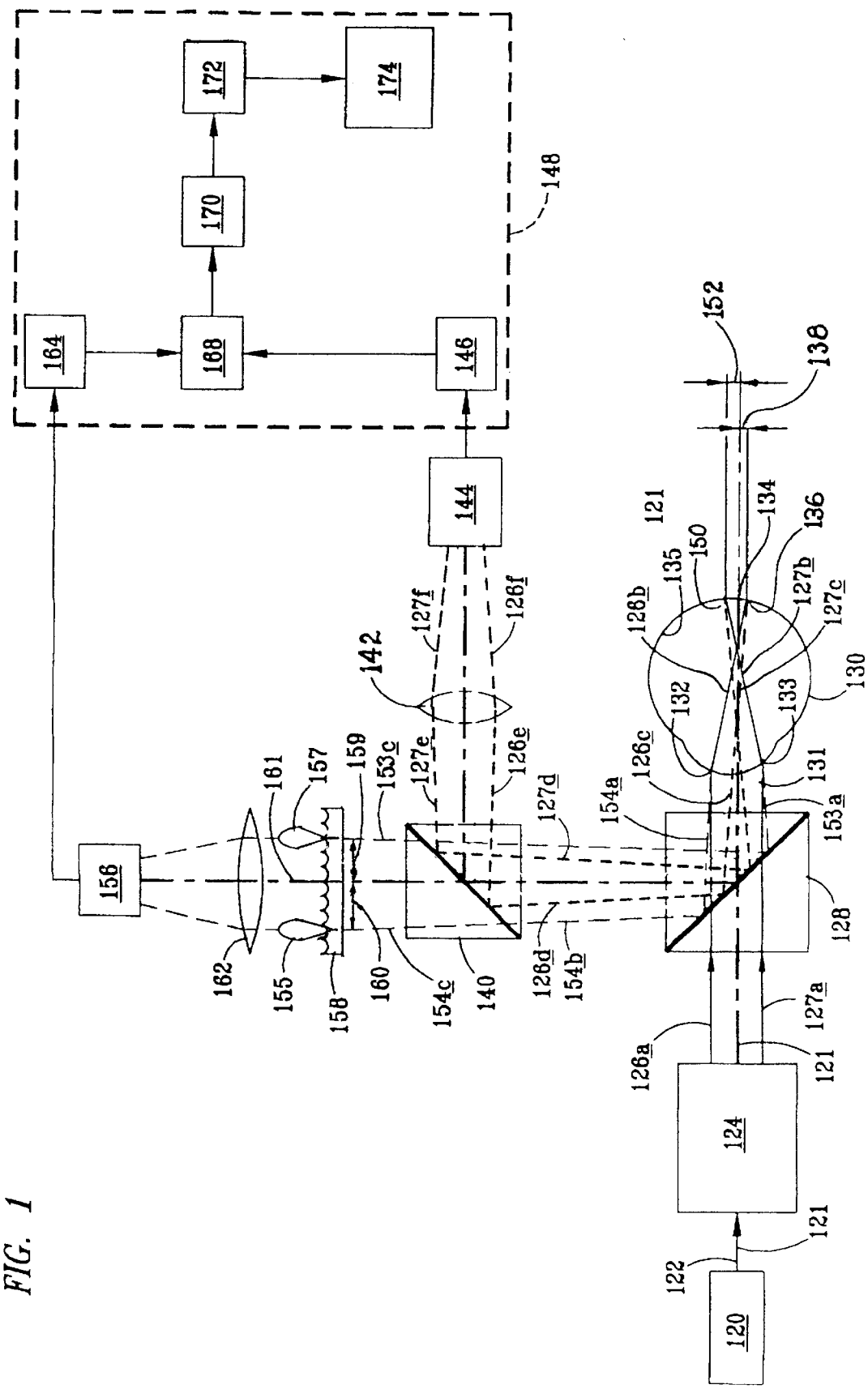
FIG. 1 is a functional schematic drawing a device for synchronous mapping of the total refraction non-homogeneity of the eye and its refractive components.

FIG. 1 shows a schematic functional view of a device and method for synchronous mapping of the total refraction non-homogeneity and components thereof according to one aspect of the present invention. A polarized light source 120 and preferably a laser light source directs a polarized light beam 122 along a polarized light beam path nominally coincident with a central eye axis. The light beam is provided to a beam shifter 124 that is controlled to rapidly shift light beam 122 to any of a plurality of spatially offset parallel light beam paths 126. The mechanism for light beam shifting will be discussed more fully below in connection with FIGS. 3 and 4. Beam shifter 124 provides a polarized probing beam 126. It will be understood that a plurality of such probing beams can be produced by beam shifter 124 within a few milliseconds as, for example, 65 spatially offset parallel polarized probing beams can be produced within 12 milliseconds. For example, only one of the probing beams may be coincident with central axis 121, another of the plurality of offset polarized probing is depicted as 127. It will be understood that, for purposes of clarity, the 65 or more parallel polarized probing beams are not depicted in FIG. 1. Each of the probing beams 126, as well as the plurality of beams 127, pass through a beam splitter 128 to the eye 130 under investigation. Each probing beam 126, 127 impinges upon the cornea 131 at a plurality of impingement points as, for example, point 132 corresponding to probing beam 126 and impingement point 133 corresponding to probing beam 127, is representative of a plurality of impingement points.

The total refractive eye aberration for a thin beam of light entering at impingement point 132 is determined by locating point 136 on the retina and determining the spatial position 138 of that illuminated point on the retina 136 relative to the fovea 134 aligned along central axis 121. This position may be indicated relative to central axis 121 by coordinates ($dx_1$, $dy_1$). Light impacting the retina is backscattered off the retina. The backscattering is not a reflection per se and therefore the entering beam 126b is depolarized by the retinal surface. The backscattered light, having its optical axis represented by path 126c, is non-polarized light. The light 126c is directed in beam splitter 128 along path 126d to a polarizing beam splitter 140. Beam splitter 140 is a polarizing beam splitter so that it reflects non-polarized light and allows polarized light to pass through it. Thus, beam 126d is directed along path 126e through a lens 142 that focuses it along path 126f to a first photo detector 144. As will be discussed more fully below with respect to FIGS. 2, 3 and 8, photo detector 144 may be provided with a further beam splitter 94 and x and y photodetection arrays 88 and 89 to determine the position ($dx_1$ and $dy_1$). From this position and based upon the standard length of the eye, the total refraction characteristics can be calculated in a total refraction calculator 146. The total refraction calculator 146 may, for example, be circuitry and/or computer software within a multifunction computer 148.

Returning now to FIG. 1, each of the plurality of offset probing beams of which 127a is a sample, passes through beam splitter 128 and impinges upon the anterior surface of the cornea 131 at a plurality of impingement points of which 133 is a representative sample. Entering at impingement point 133, the beam 127b is projected due to the total refractive characteristics of the eye along the path of beam 127 to a point 150 on the retina 135 of eye 130. The backscattered light 127c from the retina 135 is projected back out through the eye aperture and is directed by beam splitter 128 along path 127d to the polarizing beam splitter 140, where it is directed along path 127e through lens 142 and onto a first photodetector 144 for determining the offset location 152 represented by ($dx_2$, $dy_2$) away from central axis 121. Through the rapid and repeated operation of beam shifter 124, a plurality of times within a fraction of a second, an entire grid pattern of impingement points, see, for example, the grid pattern of FIG. 10. As will be more fully discussed below, mappable data, with respect to the total eye aberration is provided at the total refraction calculator 146.

Synchronously with each of the polarized probing beams 126a and the plurality of additional beams 127a, the component of aberration caused by aberrations in the cornea surface 131 may simultaneously be determined. Because beams 126*a* and 127*a* are polarized light, they will partially reflect off of the cornea surface 131 as a polarized light beam 154*a*, in the case of probing beam 126*a*, at an impingement point 132 and as reflected polarized light 153*a* in the case of probing beam 127*a* and at impingement point 133. Because the light reflects from the cornea at an angle corresponding to the angular position of the anterior cornea surface 131 at the point of impingement 132, reflected beam 154*a* diverges from beam 126*a*, depending upon the refractive characteristics of the cornea 131 at the impingement point. Beam 154 is directed by beam splitter 128 to polarizing beam splitter 140 along path 154*b*. The beam 154*b* passes through polarizing beam splitter 140 because it is polarized light that was reflected from the cornea surface and travels along path 154*c* so that its position may be detected by a second photodetector 156. To facilitate determination of the reflective angle of beam 154 off of the cornea, the distance from the cornea to a semitransparent scattering screen 158 is a known quantity so that the offset distance 160 of the beam 154*c* impacting scattering screen 158 is indicative of the topography of the cornea surface 131.

The scattering screen 158 causes, the light beams 154*c* and 153*c*, to scatter, as schematically depicted with scattering diagrams 155 or 157. The position 160 or 159, with respect to the optical centerline 161, is imaged by a lens 162 onto the second photodetector 156. Once again, the second photodetector 156 may comprise an array of x and y photodetectors using a beam divider to determine the x-y position 160 for the reflected light from the cornea. This information is provided to a cornea cause refraction calculator 164.

The data from both total refraction calculator 146 and from he cornea cause refraction calculator 164 is fed into a comparator 168 and also to memory 170. The comparator information produces data, including the total refraction for each point, the cornea cause refraction for each impingement, i.e., for each shifted probing beam and may also determine the component of the refraction aberration due to components of the eye other than the cornea. From this information, a map of refractive characteristics of the eye is reconstructed in a map reconstruction unit 172. The reconstruction map produced at 172 may be displayed at a display 174, such as a CRT screen or a color printout. All of the total refraction calculator 146, the cornea cause refraction calculator 164, the comparator 168, the memory 170, the map reconstruction unit 172 and the display 174 may be separately provided or alternatively may be included in a computer system and display screen and/or printer schematically represented by system dash lines 148 in FIG. 1.

Figure 2:
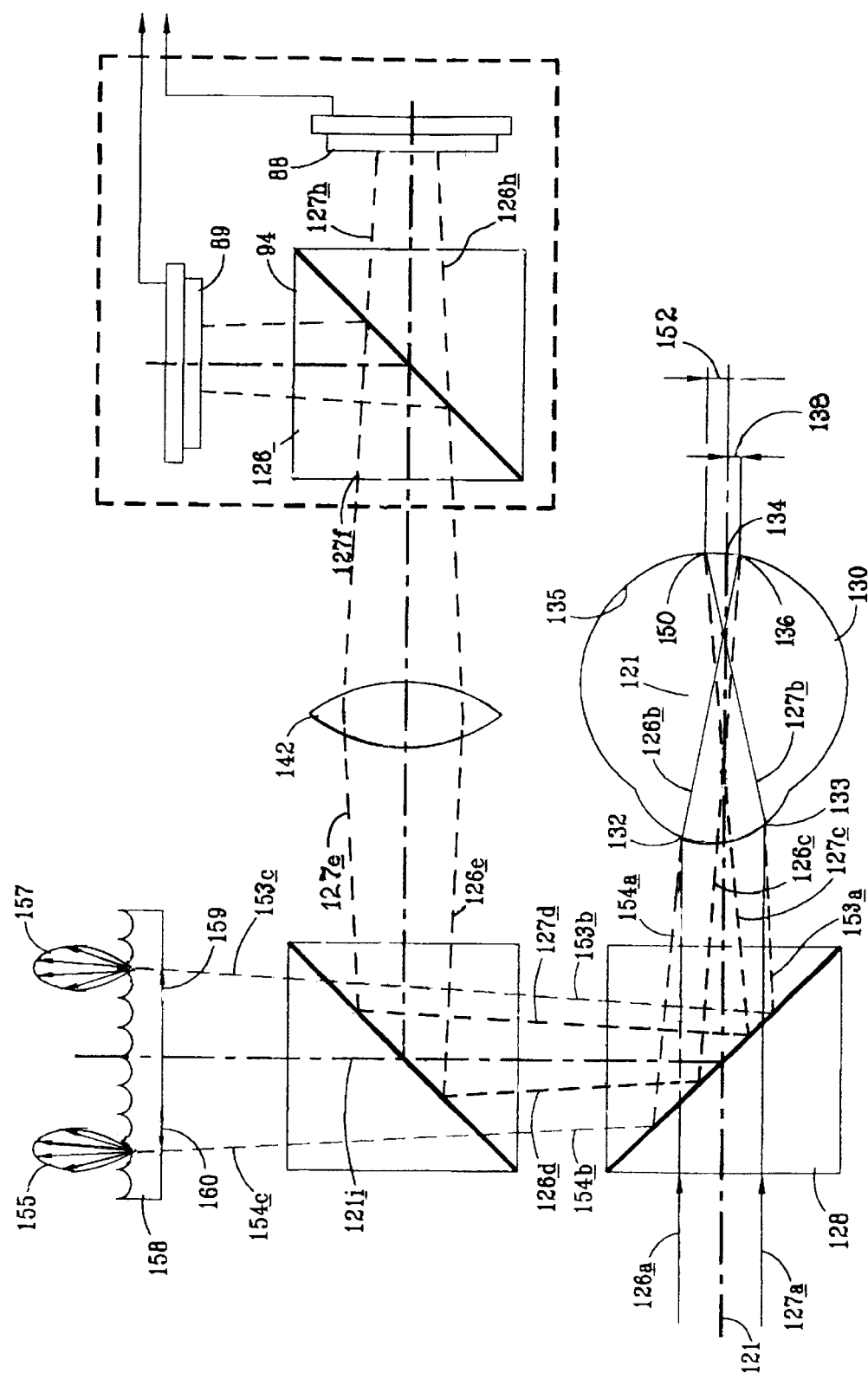
FIG. 2 is a schematic depiction of an eye under investigation in which the theoretical aspects of the total eye refraction determination and also the corneal component of refraction may be more fully understood.

FIG. 2 is an enlarged schematic view of a portion of the device for synchronous mapping of the total refraction and its component parts, better schematically depicting the paths of the probing beams 126*a* and 127*a*, as well as the backscatter light path 126*c*, 126*d*, 126*e* and 126*f* to a photodetector 146. The photodetector 146 is shown comprising an x component detector 88 and a y component detector 89. Further, the beams respectively directed or passing through the polarizing beam splitter 140 are more clearly depicted and the points of impingement on the semitransparent light scattering screen 158 are more clearly demonstrated.

The semitransparent light scattering screen 158 may, for example, be milk glass or translucent fluorescent light cover material having a substantially homogeneous characteristics so that polarized light beams impacting at any point produce the same relative intensity and same relative diffusion by which the position of such light beams may be detected with position sensor 156. The second position sensor 156, although not depicted, may also be constructed similarly to position sensor 146 so that x component sensor array 88 and y sensor component array 89 are used in combination to get an x-y position sensor.

Figure 3:
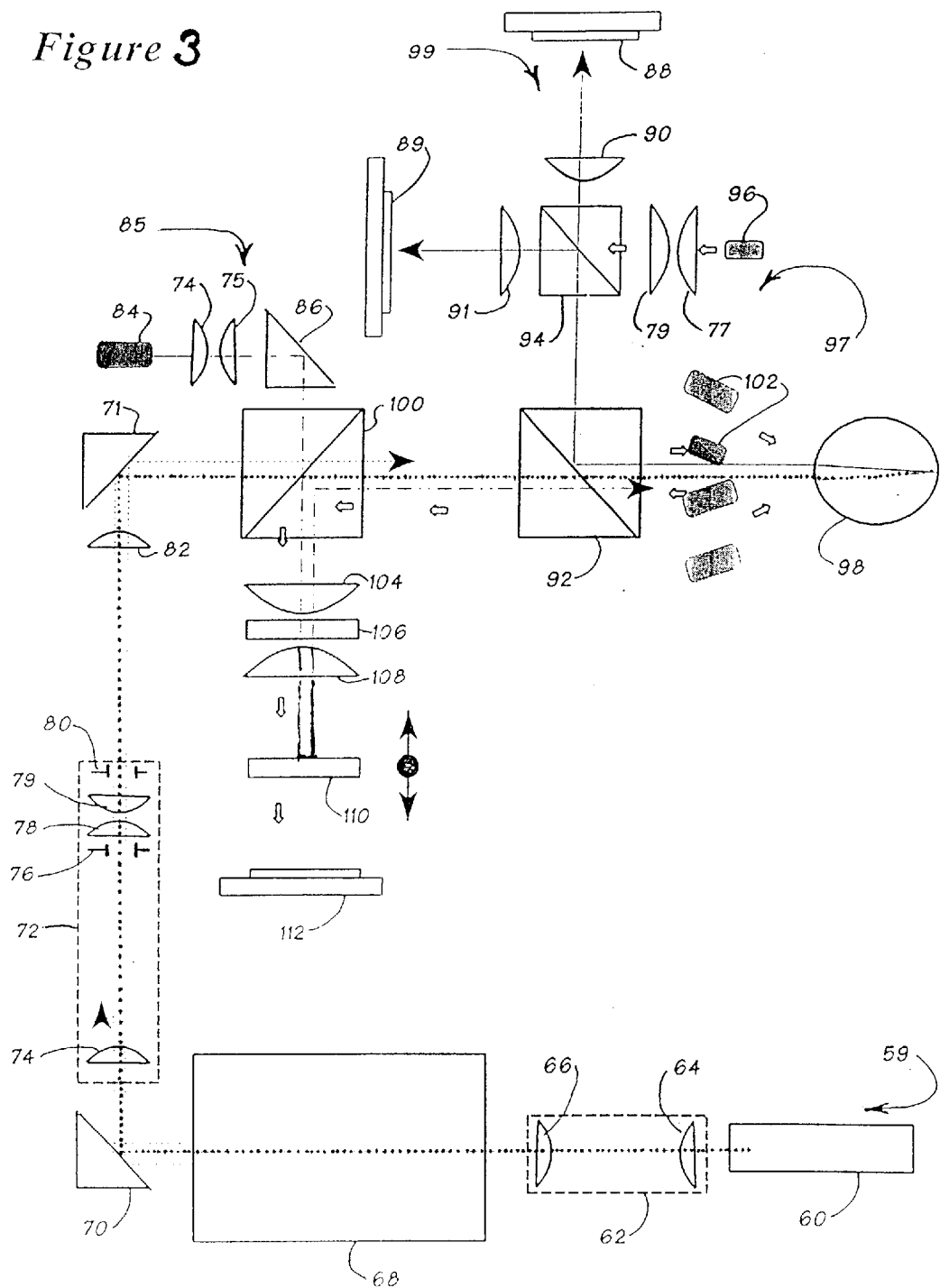
FIG. 3 is a schematic diagram of a preferred alternative embodiment of an aberration refractometer according to certain aspects of the present invention.

FIG. 3 schematically depicts the optical channels of one embodiment of the total aberration portion of the refractometer of the subject invention. A spatially defined parallel beam input channel 59 extends from a light source such as a laser or other low diffusion light source up to the eye of a patient 98. In one preferred embodiment a 650λ laser was employed. Along the spatially-defined parallel beam input channel is a cylindrical telescope 62 including two lenses 64 and 66. Light from the cylindrical telescope enters the deflector 68. The deflector 68 is preferably an acousto-optical deflector electronically controlled by a control unit such as a computer. Alternatively a galvanometric mirror deflector or the like could be used. Two coordinate deflectors or angular direction mechanisms may be used as a deflector 68. A reflection mirror or mirror prism 70 reflects the light beam through a telescopic system 72, including preferably, but not necessarily, a lens 74, an entrance aperture 76, lenses 78 and 79 and an exit aperture or field stop 80. The polarized light beam passes from the field stop 80 to collimating lens 82 and is deflected by mirror 71 and passes transparently through beam splitter 100 and interferential beam splitter 92 en route to the eye 98.

Light sources placed in front of the eye are used to align the visual axis of the eye with the optical axis of the instrument. Preferably a plurality of orthogonally placed light emitting diodes (LEDs) 102, for example emitting at a λ of 940 mm could be employed. Light produced by LEDs 102 is reflected off the cornea and imaged by camera 112. When the reflected light aligns with preset targeting parameters, the instrument is in the proper alignment and therefore in the permissive mode for firing of the spatially resolved parallel beams formed along channel 59.

The illuminated eye is then ultimately imaged by camera 112 as the image passes through the beam splitter prism 92 and is redirected at beam splitter 100 to pass through optical elements 104, 106, 108 and 110 to finally fall upon the CCD camera 112.

A retinal spot position detecting channel 99 is used to detect the position of reflected spots from the retina of eye 98 created by the input channel and includes a interferential polarization beam splitter 92 that directs non-polarized reflected light from the retina of eye 98 to a position sensor.

In one embodiment of a photodetection position sensor as shown in FIG. 3, there is a beam splitter 94 that splits the image directing one component of the nonpolarized retina image through an optical lens 90 to a "x-coordinate" photodetector 88 and directs another component of the image through optical lens 91 to a "y-coordinate" photodetector 89. Preferably, the orthogonally placed photo detectors 88 and 89 are high resolution linear array photodetectors and the position measurement created on those detectors may be used directly to provide XY coordinates for the measurement of the position of reflected spots on the retina of eye 98. Instead of using linear array detectors, an actual XY matrix photo detector or a CCD detector with its own objective lens can be used to replace the beam splitter 94 lenses 90 and 91 and the linear array photodetectors 88 and 89. One benefit of the linear arrays is that they provide for a large range of aberration detection that exceeds the range of a simple quadrant photodetector. For example, a typical quadrant photodetector may be useful for detecting aberrations of a range of about ±3 diopters while linear arrays can accommodate a range of approximately ±10 diopters. Another option is to use lateral position sensing detectors. The drawback of using a quadrant detector is in the dependence on the shape and size of the light spot imaged on its surface. Multi-element detectors like 1D or 2D arrays (linear arrays or CCD) as well as lateral position sensing detectors are free of this drawback. In yet another embodiment, the photo detector may be a 2-dimensional or x-y photodetection matrix or a CCD sensory matrix.

Figure 11:
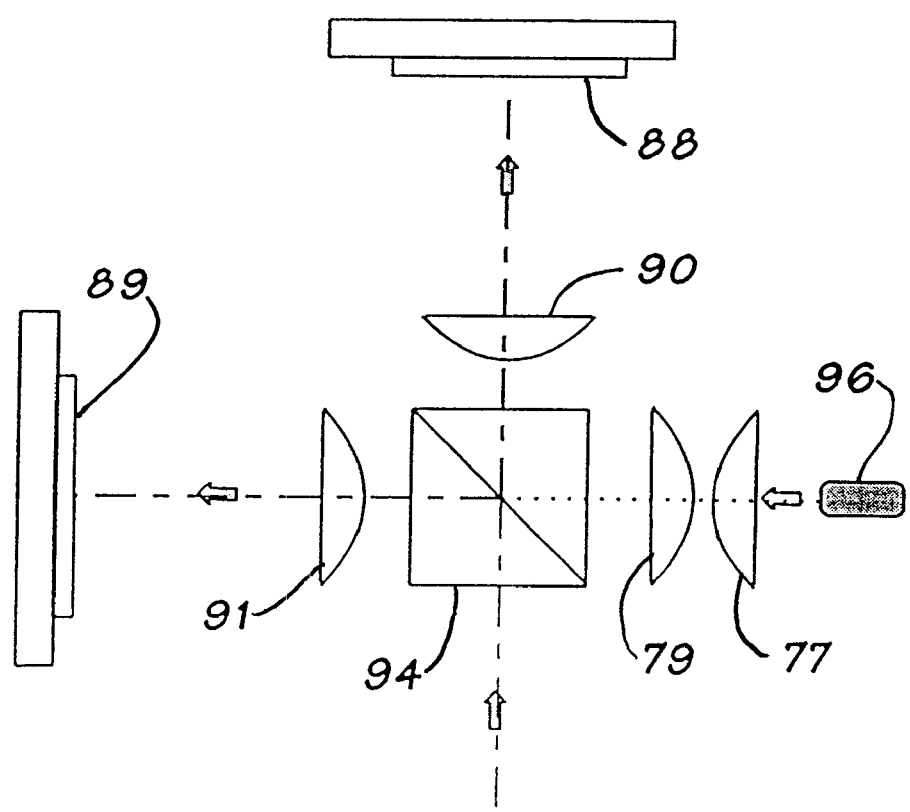
FIG. 11 is a schematic illustration of a photodetector using linear array detector components.

Details of the embodiment depicted in FIG. 3 are further explained with reference to FIG. 11 below. The position of a spot of targeting light reflected back from a reflection spot on the fovea of the retina can be determined using reflection beam splitter 94 to direct a first portion of the reflected nonpolarized light from the retina spot through lens 90 to an x-direction linear array photodetector 88 for measuring changes in position only in one direction, for example in a x-direction. A second portion of the reflected nonpolarzed light, substantially identical to the first portion, is directed through lens 91 to a y-direction linear array photodetector 89 for detecting changes in position only in a direction at ninety degrees to the first direction, for example the y-direction. The change in the x-y position is measured by calculating the position of the center of light intensity of the light spot projected on the linear array 88 (x direction) and linear array 89 (y direction).

Light source 96 and condenser lenses 77 and 79 enable homogeneous irradiating of the linear arrays 88 and 89, thus checking their homogeneity at servicing. Light emitting diode 96 and condenser lenses 77, 79 form a wide beam for calibrating photodetectors 88 and 89. If any of the elements is out of tolerance, its output can be corrected at signal processing procedures.

A fixation target channel 85 preferably comprises a light source. In a preferred embodiment the light source is a green 565 λ LED 84. The light may be transmitted through lenses 74 and 75 and directed by prism 86 and through beam splitter 100 which has wavelength differentiating optical coatings. Fixation target is positioned on the optical element 106. The light beam from LED 84 passes through lenses 104 and 108 and fixation target 106 and is reflected off of the mirror 110. The fixation target light passes back through the lens 104 and is redirected by beam splitter 100 at 90 degrees out toward the eye for the patient to visualize the image as coming from the location of the surface 110 which image can be moved from near fixation to far fixation or adjustable anywhere in between and this may be used for changing the eye accommodation over a period of time and simultaneously taking a series of measurements including spatially resolved aberration refraction measurements as well as pictures on the CCD camera 112. This produces a time lapse imaging of the eye and measurements of the aberration refraction as it cycles through different fixation target distances. The different target fixation distances may be automatically moved or adjusted from near to far using electro mechanical adjustment means that may be synchronized with the measurements and/or images taken on a time lapse basis.

The instrument described herein was developed to provide a total aberration refractometer able to accurately and quickly provide a refractive map of either emmetropic or ametropic eyes without accommodation error.

Figure 4:
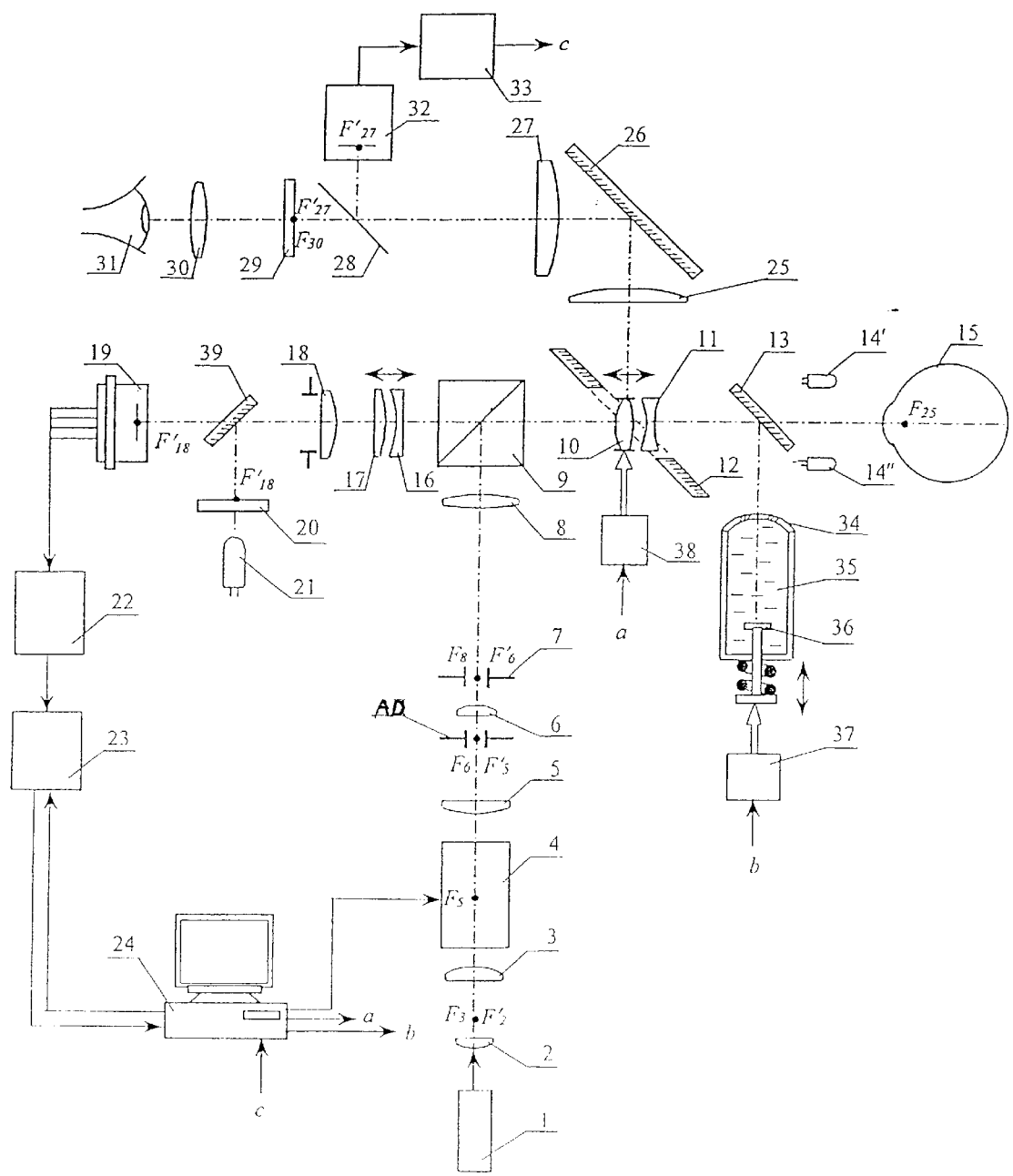
FIG. 4 is a functional schematic diagram of an instrument for measuring total aberration refraction.

FIG. 4 shows a functional diagram of another embodiment of the subject instrument for measurement of the total aberrations in the eye and total refraction non-homogeneity. A light source whose radiation is used for the ray tracing of the eye is provided, as for example, by laser 1. A telescopic expander comprising for example lenses 2 and 3 provides a normal functioning of a two-coordinate acousto-optic deflector 4 preferably consisting of two single-coordinate deflectors. A telescopic laser-beam narrower is formed by lenses 5 and 6 with an aperture stop or diaphragm AD located at the common foci of the lenses 5 and 6. A field stop or diaphragm 7 is placed at the back focus of lens 6 so that its image formed by the telescopic narrower in the back-pass is located between the single-coordinate deflectors. With this placement, the redistribution of the light illuminance in the light spot on the pupil is minimized when the angular position of the laser beam is varied at the exit of the single-coordinate deflectors. The front focus of a collimating lens 8 is aligned with the center of the field stop or diaphragm 7 to ensure telocentric passage of rays through interferential polarizing beam splitter 9.

An ametropia compensator is schematically depicted as a varifocal group of lenses 10 and 11, adjustable to compensate for the patient's eye ametropia. One of the lenses is mounted on a movable base connected to actuator drive 38. An accommodation controller is schematically depicted as lenses 16 and 17 that constitute a varifocal group of lenses for accommodation control of the patients eye.

An objective lens 18, at whose focal point the photosensitive surface of a position-sensitive photodetector 19 is located, is intended to form an image of the irradiated retina in the plane of the photosensitive surface of the position-sensitive photodetector. The photosensitive elements of the photodetector are connected through a preamplifier 22 and an analog-to-digit converter 23 to a computer 24. A beam coupler 39 is movably mounted between the objective lens 18 and the photodetector 19 to optically conjugate the plane of the test-target or plate 20 with the photosensitive surface of the first photodetector 19 as well as with the fovea surface. The plate 20 is needed to ensure the fixation of the patient's gaze. Located behind the plate 20 is a light source or radiator 21 serving to illuminate the plate.

Elements 25 through 30 comprise a microscope whose objective lens consists of lenses 25 and 27 together with mirror 26. A plate 29 with first coordinate-grid is preferably located at the back focal plane of a lens 27. A lens or a group of lenses 30, the front focal point of which coincides with the back focal point of the lens 27, comprises an eyepiece of the microscope. The beam splitter 28 serves to optically couple the retinal plane with the photosensitive plane of a TV camera 32 connected to the computer through a video signal conversion and input board, alternatively termed a frame grabber board, 33.

By means of a mirror 12 provided with an opening, the optical axis of the microscope is aligned with the optical axes of the ray tracing channel (elements 1–11) and the photoelectric arrangement for measuring the transverse ray aberration on the retina (elements 16–19).

In a preferred embodiment, four light-emitting diodes (LEDs) 14 are installed in a cross-wise configuration in front of the patient's eye. Each LED is preferably located in the same plane as each other LED, at an equal distance from the optical axis and perpendicular with the axis. The microscope and the LEDs comprise a system for the visual and television positioning of the instrument relative to the patient's eye. The microscope is installed so that the front focal plane of lens 25 coincides with the plane, where imaginary or virtual images of the LEDs 14, mirrored by the anterior corneal surface, are located.

Before the total refraction measurement process is commenced, the instrument is positioned relative to the patient's eye and the instrument is calibrated using the optical calibration unit 34–36. Movably mounted between the lens 11 and the LEDs 14 is a mirror 13 which serves to join the optical axes of the instrument and the optical calibration unit 34–36. In one preferred embodiment of an optical calibration unit, it comprises a meniscus or cornea simulator 34, liquid medium or vitreous simulator 35, and retina simulator 36. The retina simulator 36 is preferably movably mounted so that it can be moved along the optical axis by means of actuator or drive 37.

The instant measuring instrument incorporates a computer 24 or like device for controlling the acousto-optic deflector 4, analog-to-digital converter 23, and actuators or drives 37 and 38. The computer 24 or like device or devices may perform additional duties including, for example, mathematical processing and data storage, calculation and display of aberration parameters and the ocular refraction characteristics as well as provide setting measurement modes and implementation of automatic instrument alignment.

The instrument for measurement of the total eye refraction, in its preferred embodiment, functions in the following way. The light beam emitted, for example by laser 1, is expanded, collimated and directed to the acousto-optic deflector 4, which changes its angular position in accordance with the corresponding computer program. The telescopic narrower 5 and 6 reduces the beam thickness to the requisite magnitude. The center of the stop or diaphragm 7 is a point of angular "swinging" of the beam exiting from the telescopic narrower. Due to its positioning in the front focal plane of the lens 6, the aperture stop or diaphragm AD has its image in the back focal plane of the lens 8 which is aligned with the eye pupil. Further, because the stop or diaphragm 7 is positioned in the front focal plane of the collimating lens 8, angular swinging of the laser beam with the angle vertex located on the stop or diaphragm 7 is converted into parallel shifting of its optical axis after passing the lens 8.

If the patient's eye is ametropic, the axial movement of the lens 10 (or 11) converts the telocentric beam into a beam which diverges (in the case of myopia), or converges (in the event of hyperopia), so that the image of the diaphragm 7 is optically conjugated with the retina. This also ensures parallelism of the rays reflected by the retina in the zone in front of the beam splitter 9, which is necessary for its normal functioning.

The light entering the eye 15 of the patient is polarized in the plane shown in FIG. 4. Only that component of the returning beam depolarized by interaction with the retina is allowed by the beam splitter 9 to pass to the first photodetector 19. This protects the first photodetector from the polarized light reflected by the surfaces of the lenses 10 and 11 and by the cornea or the eye and which can produce an illuminance incompatible with determining the total refraction according to normal functioning of the instrument.

Lenses 16 and 17 and the objective lens 18 produce an image of the illuminated area of the retina in the plane of the first photodetector 19. In FIG. 4 the foci locations are designated as follows: $F_3$, $F_5$, $F_6$, $F_8$, $F_{25}$, and $F_{30}$, designating points of front foci of the corresponding lenses while $F_2'$, $F_5'$, $F_6'$, $F_{18}'$, and $F_{27}'$, designating points of back foci of the lenses.

Figure 5:
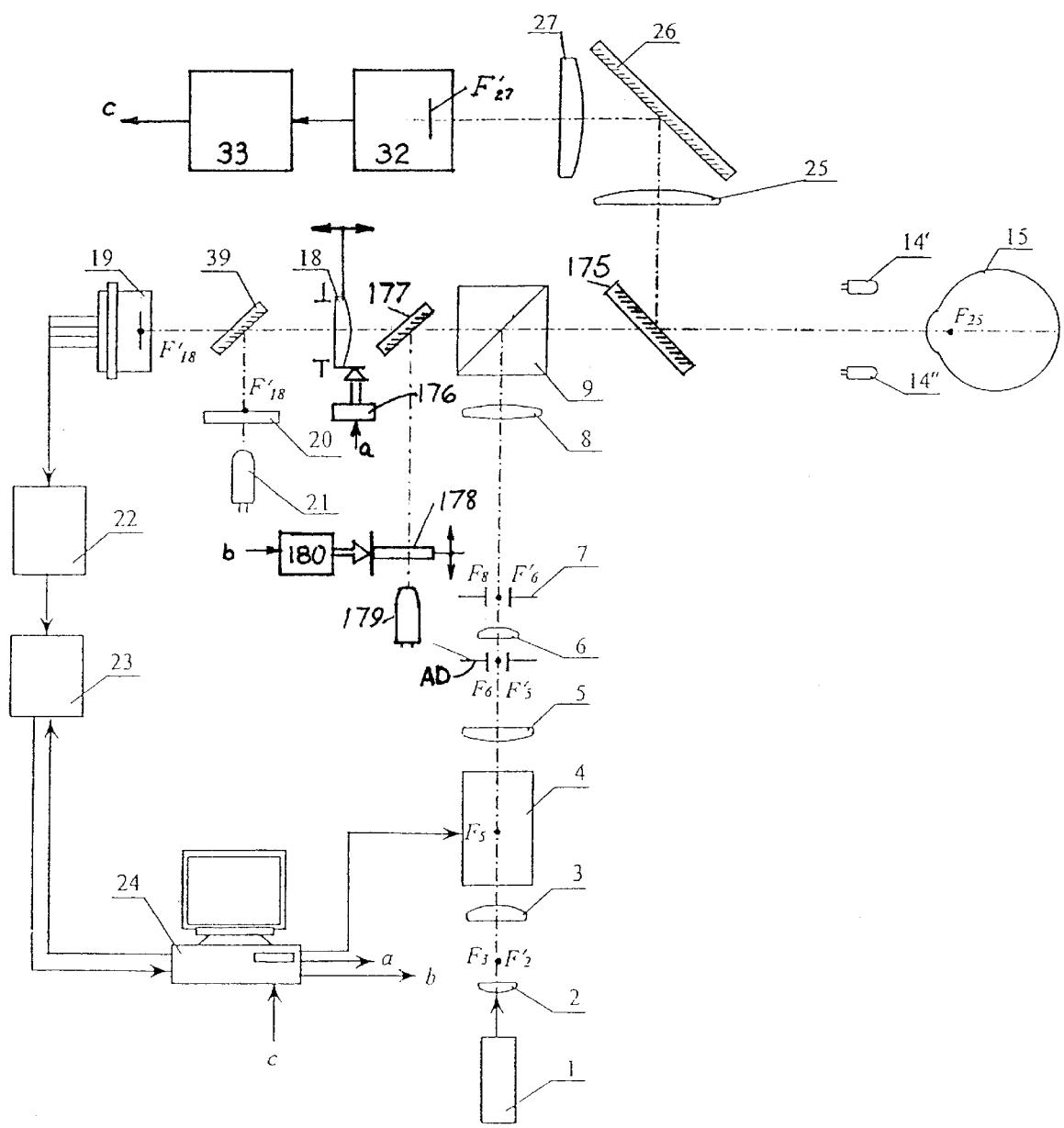
FIG. 5 is a schematic illustration of the operation of one embodiment of a device for measuring the total transverse aberration of a laser beam on the eye retina.

In one more embodiment, presented in FIG. 5, the function of ametropia compensator is combined in the component 18 that is an objective lens for the photodetector 19. In this embodiment, target object 20 and photodetector 19 are positioned at equal distances from the lens 18. LED 21 irradiates the target object 20. The lens 18 is positioned by the patient in such a way that a clear image of target object 20 is seen. In this position, focal planes of the photodetector 19 and the eye 15 are conjugated. Positioning of the lens 18 can be implemented with the electric drive 176. This positioning can be done automatically. Accommodation control is executed with another target object 178, irradiated by the LED 179, and positioned by an electronic drive 180. Both drives, 176 and 180, are connected with computer 24. Accommodation target object 178 is coupled with optical axis by the mirror 177. Colors of LEDs 21 and 179 should be different for their easy identification. For example, conjugation is made with red LED 21, and accommodation follows with green LED 179.

Figure 6:
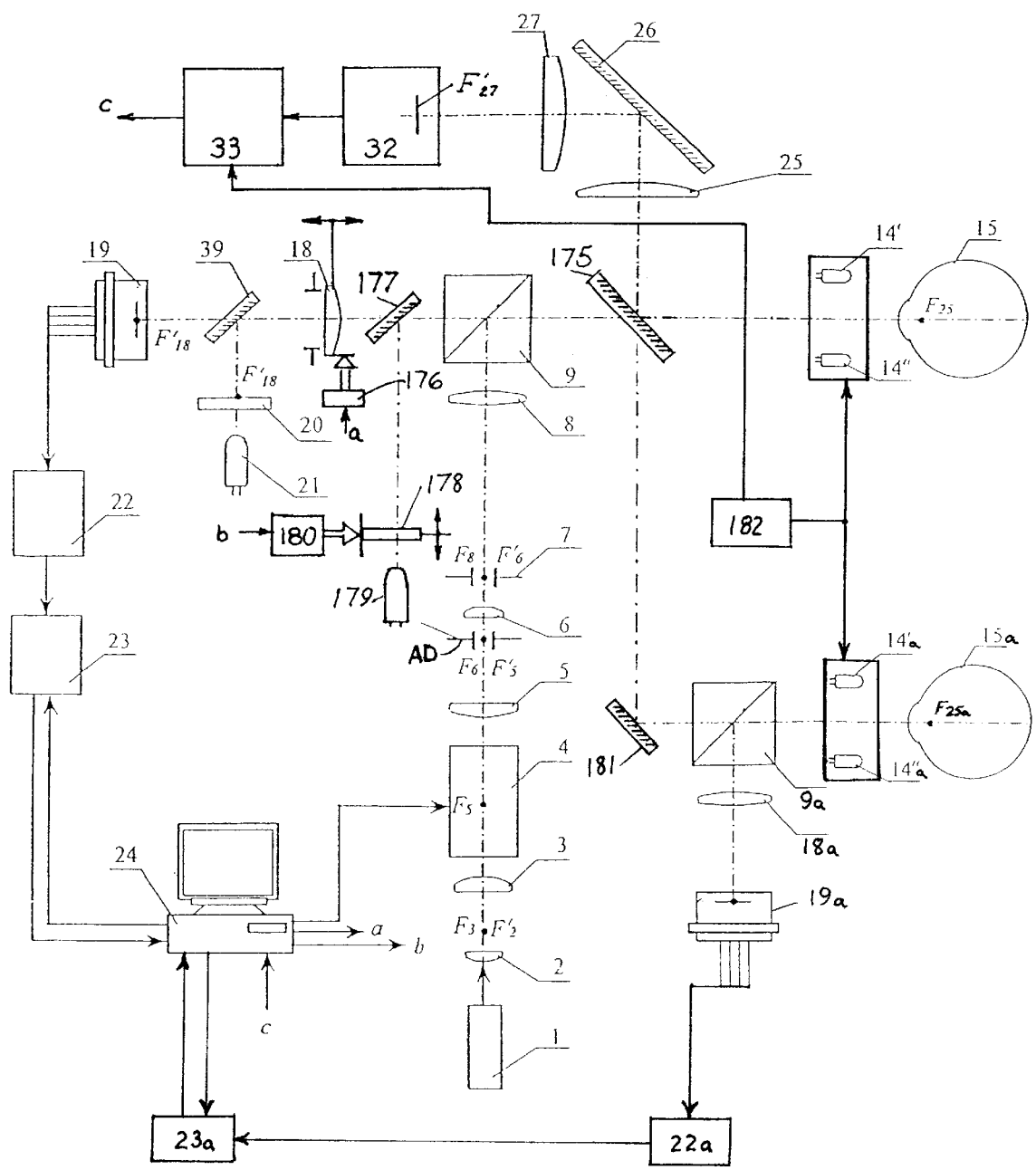
FIG. 6 is a schematic illustration of the operation of another embodiment of a device for measuring the total transverse aberration of a laser beam on the eye retina.

Still another embodiment of the invention, schematically shown in FIG. 6 and based generally on the configuration presented in the FIG. 5, enables simultaneous investigation of both eyes 15 and 15a. According to the design shown in FIG. 6 this embodiment beneficially contains an additional channel for the second eye 15a. The implementation is such that the common laser probing is used for both eyes due to two beam splitters 175 and 181. Optical and electrical components 9a, 14a, 18a, 19a, 22a, and 23a have the same roles as the corresponding components 9, 14, 18, 19, 22, and 23 at measurement of the first eye 15. Control unit 182 switches the infrared LEDs 14 and 14a to alternatively get irradiated first and second eye 15 and 15a respectively. In this way, images of the eyes can be displayed simultaneously, for example, on the left and right parts of the monitor's screen. Described implementation enables separate adjustment and advantageously provides simultaneous measurements on both eyes.

In the various embodiments of FIGS. 4, 5, and 6 the laser beam is positioned by the computer and the acousto-optic deflector so as to enter the pupil within the requisite refraction measurement zone. If the optical system of the eye has aberration refraction, the light image of the stop or diaphragm 7 on the retina is displaced from the axis, which results in the corresponding displacement of the illuminated zone image on the photosensitive surface of the position-sensing photodetector 19.

If photodetector 19 is a four-quadrant photodiode, as, for example, that shown diagrammatically in FIG. 7, having quadrants 1, 2, 3 and 4, an aberration displacement of the light spot δx, δy on the retina can be given by the formula:

$$\delta x = \frac{\beta}{2}\left[\frac{(U_1+U_4)-(U_2+U_3)}{U_1+U_2+U_3+U_4}\right]\cdot b,$$

$$\delta y = \frac{\beta}{2}\left[\frac{(U_1+U_2)-(U_3+U_4)}{U_1+U_2+U_3+U_4}\right]\cdot b,$$

where β is the transverse magnification in the plane of the first photodetector as related to the plane of the retina, b is a coefficient depending on the size of the light spot in the plane of the photodetector, and $U_1$, $U_2$, $U_3$ and $U_4$ are the photoelectric signals coming from the corresponding photodetector channels.

If photodetector 19 is a lateral position sensing detector, as shown in FIG. 8, having a pair of x-direction electrodes 1 and 2, and a pair of Y-direction electrodes 3 and 4, an aberration displacement of the light spot δx, δy on the retina can be described as follows:

$$\delta x = \beta \left[ \frac{U_1 - U_2}{U_1 + U_2} \right] \cdot a,$$

$$\delta y = \beta \left[ \frac{U_3 - U_4}{U_3 + U_4} \right] \cdot a,$$

where $\beta$ is the transverse magnification between the planes of photodetector and retina, $U_1$, $U_2$, $U_3$ and $U_4$ are the signals coming from the electrodes, 1, 2, 3 and 4 correspondingly, and a is a scaling coefficient depending on the electrical parameters of the lateral detector.

The principle of operation relating to the positioning the instrument in relation to the patient's eye is illustrated in FIG. 9. The collimating system 50 corresponds to the elements 39, 18 and 17, 16 of FIG. 4 (if the eye is accommodated at a finite distance). Point A is the light radiator and gaze fixation point and is formed by the elements 20 and 21 in FIG. 4. The mirror 56 with an opening corresponds to element 12 of FIG. 4. The microscope objective lens 52 is comprised of the elements 25–27 of FIG. 4 while the microscope objective image plane 54 (FIG. 4) corresponds to the element 29 (FIG. 4). $B_1$ and $B_2$ are light radiators corresponding to the LED 14 of FIG. 4. $B'_1$ and $B'_2$ are primary images of the radiators while $B''_1$ and $B''_2$ are secondary images of the radiators.

As can be seen from FIG. 9, the fixation of the gaze on the point A, located on the optical axis of the instrument, does not guarantee the coincidence or alignment of the visual axis of the eye and the optical axis of the instrument because the eye sees the point A on the fovea even when $\Delta \neq 0$. The fixation of the gaze on the point A is ensured only when the above axes are parallel.

Taking into account that the largest contribution to the optical power of the eye is made by the anterior surface of the cornea, the visual axis line is assumed to be the line passing through the fovea center and the vertex of center of curvature of the front surface of the cornea. If the radiator $B_1$ is positioned in front of the patient's eye, then, due to reflection of the light from the anterior or front surface of the cornea, this surface functioning as a convex mirror, forms an imaginary or virtual image $B'_1$ of the radiator, located symmetrically to the axis in accordance with the laws of geometric optics.

When several radiators, such as for example, $B_1$ and $B_2$, are positioned in front of the patient's eye symmetrically to the optical axis of the instrument (FIG. 9), their secondary images $B''_1$ and $B''_2$ will be shifted in the image plane of the microscope objective lens aside from the axis if $\Delta \neq 0$.

Thus, to make the optical axis of the instrument and the visual axis of the eye coincide, two conditions must be satisfied: the patient's gaze is fixed on the point A and the images $B''_1$ and $B''_2$ are centrally positioned in relation to the axis of the objective lens 52. The positioning can be checked using the coordinate grid provided on the plate 29 (FIG. 1) or using the monitor screen when the TV channel is utilized. When the image of the eye is aligned at all points with concentric locations on the grid or the TV screen, the measurement controller is armed for taking a spatially resolved set of refraction measurements. The operator can than activate the measurement that can take only a few milliseconds. The measurements are "grabbed" in the grabber board and stored for producing an aberration refraction map as in FIG. 12. The measurements can also be activated automatically when the proper alignment is detected. Further, according to one embodiment of the invention, a plurality of measurements can be made sequentially during the occurrence of a predetermined event, such as through a sequence of movement of the eye target from a "near" accommodation distance to a "far" or infinity accommodation distance. A plurality of measurement images can be captured or automatically grabbed and stored over a time period or while any other changes are occurring for which eye measurements might indicate a dynamic change in the refraction of the eye.

The coincidence of the points $B''_1$ and $B''_2$ with the surface or plane 54 is indicative of setting the fixed working distance between the instrument and the eye which is the result of the focusing of the images $B''_1$ and $B''_2$ on the surface 54.

The point of gaze fixation is created by locating the mirror 39 (FIG. 4) on the optical axis of the instrument. The radiators 14' and 14" play the part of the radiators $B_1$ and $B_2$ shown in FIG. 9.

Another embodiment of eye instrument alignment can be implemented using manually or automatically operated measurement of the pupil edges; forming a figure, approximately a circle. Its center does not coincide usually with the center of symmetry of four reflexes, two of which $B''_1$ and $B''_2$ are shown in FIG. 9. This non-coincidence can be taken into consideration at further signal processing.

The calibration of the instant aberration refraction instrument may be effected using the optical calibration unit. The optical calibration unit can be made to incorporate known aberrations at the corresponding cornea simulator 34 measurement points. For example, the aberration may be determined by the computer using special optical design programs. If, for example, the front surface of the lens 34 is ellipsoidal, then the aberration refraction at all the points of the pupil is equal to zero.

When an ametropy compensator is used, nonparallel laser beams will enter the optical calibration unit. This will result in a standard aberration of defocusing; to compensate for this aberration, the retina simulator can be moved along the optical axis by means of the actuator 37 to the focus point. Thereby, the fovea can be optically conjugated with the retina simulator.

Systematic errors of measurements of the transverse aberration will be evidenced by the deviation of the measurement results from the estimated data. Such determinable systematic errors can be taken into account when measuring actual total ocular aberrations.

The calibration by comparison with the optical calibration unit is preferably performed automatically before measuring the ocular aberrations by locating the mirror 13 on the optical axis of the instrument.

Prior to the ray tracing of the patient's eye the mirrors 13 and 39 are withdrawn from the light path entering the eye and then the light passes to the photodetector. The aberration displacement of the image of the light spot on the fovea is measured at a set of points on the cornea corresponding to an ocular ray tracing grid chosen by the operator. An example of a grid or an allocation of measurement points on the pupil is shown in FIG. 10.

The data on measurement of the transverse aberrations on the retina $\delta x$ ($\rho$, $\phi$) and $\delta y$ ($\rho$, $\phi$) are used for further calculations of the coefficients of the Zernike polynomials by means of the least squares method in order to approximate the function of the total wave aberration of the eye. The wave aberration function is then used to calculate the local total refraction at any point of the pupil. In addition, the approximation makes it possible to determine or reconstruct the nature of local aberration refraction in that small axial zone of the pupil, where it is impossible make accurate direct measurement of refraction.

In one experiment conducted using this instrument in which five replicate tests were performed and the results averaged, the laser beam total aberration on the retina at 65 points of the pupil was been performed in within 12 milliseconds with no more that 5 mW of light radiation entering the eye.

Figure 12:
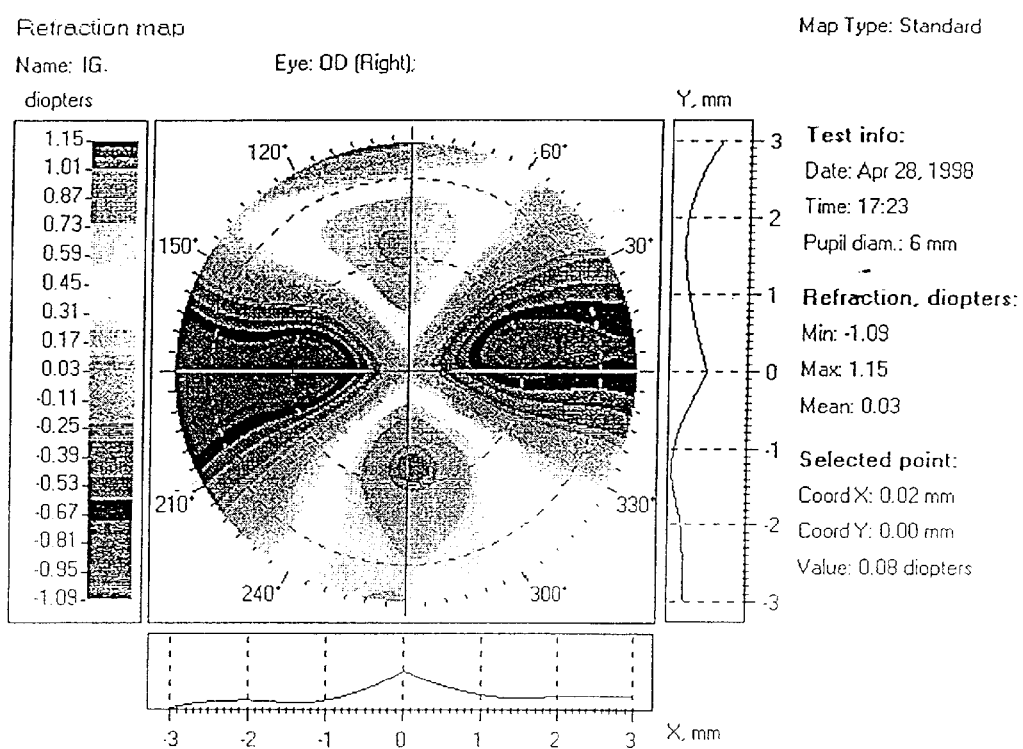
FIG. 12 is an example map showing the total aberration refraction of the eye, under consideration, constructed with the eye total aberration refractometer portion of the subject invention.

FIG. 12 is an example of an ocular aberration refraction map constructed with the use of the total eye aberration refractometer portion of the invention.

The extremely fast measurement permits the computer control program to cause a plurality of spatially resolved aberration measurements to be made in a very short period of time. The control program in one embodiment automatically activates a plurality of measurements coordinated with a series of adjusted accommodation fixation distances and automatic determination of proper eye alignment to receive a series of data measurements from the retinal spot position detecting channel. A series of refraction measurements for a dynamic eye refraction system is produced. Spatially resolved refraction measurements can be automatically programed and automatically made during a variety of dynamic changes such as varying accommodation or during normal functioning of the eye under a variety of predetermined conditions and internal or external changing conditions.

References
1. M. S. Smirnov. Measurement of wave aberration of the eye. *Biofizika* (*Biophysics USSR*), 6, pp. 776–794, 1961.
2. Van den Brink. Measurement of the geometrical aberrations of the eye. *Vision* Res. 2, pp. 233–244, 1962.
3. N. M. Sergienko. *Oftalmologicheskaya optika* (*Ophtalmic Optics*). Moscow, Meditsina, 1991, 142 pages.
4. R. H. Webb, C. M. Penney, and K. D. Thompson. Measurement of ocular local wavefront distortion with a spatially resolved refractometer. *Applied Optics*. 31, pp. 3678–3686, 1992.
5. S. G. El Hage and Bemi F. Contribution of the crystalline lens to the spherical aberration of the eye. J. Opt. Soc. Am. 63, pp. 205–211, 1973.
6. J. Liang. A new method to precisely measure the wave aberrations of the human eye with a Hartmann-Shack wave-front sensor, *Ph. D. Dissertation*, University of Heidelberg, Heidelberg, Germany, 1991.
7. J. Liang, B. Grimm, S. Goelz, and J. F. Bille, Objective measurement of wave aberrations of the human eye with the use of a Hartmann-Shack wave-front sensor. *J Opt. Soc. Am. A* 11, pp. 1949–1957,1994.
8. J. Liang and D. R. Williams. Aberrations and retinal image quality of the normal human eye. *J Opt. Soc. Am.* A 14, pp. 2873–2883,1997.
9. J. Liang, D. R. Williams, and D. T. Miller. Supernormal vision and high resolution retinal imaging through adaptive optics, *J. Opt. Soc. Am.*, A 14, pp. 2884–2892, 1997.
10. U.S. Pat. No. 5,258,791. Spatially resolved objective autorefractometer, Nov. 2, 1993.
11. T. Seiler, P. J. McDonnell, "Excimer laser photorefractive keratectomy", *Surv. of Ophthalm.*, 40, pp. 89–118, 1995.

While this invention has been described with reference to illustrative embodiments, this description is not intended to be construed in a limiting sense. Various modifications and combinations of illustrative embodiments, as well as other embodiments of the invention, will be apparent to persons skilled in the art upon reference to the description. It is therefore intended that the appended claims encompass such modifications and enhancements.

Other alterations and modifications of the invention will likewise become apparent to those of ordinary skill in the art upon reading the present disclosure, and it is intended that the scope of the invention disclosed herein be limited only by the broadest interpretation of the appended claims to which the inventors are legally entitled.

What is claimed is:

1. A device for measuring aberration refraction of an eye, comprising: a polarized light source producing a probing beam along a path to the eye; a telescopic system of lenses having an entrance pupil and an exit pupil; a two-coordinate deflector consisting of two single-coordinate deflectors separated by a zone; a deflection control unit; an aperture stop; a field stop; a collimating lens; a first position-sensitive photodetector with an objective lens operatively positioned for receiving non-polarized light reflected from the retina of the eye, a second position-sensitive photodetector for simultaneously receiving polarized light reflected from the cornea of the eye; and a data processing and display unit including a computer coupled to said first and second photodetectors for calculating total eye refraction aberration and the component caused by cornea aberration.

2. The measuring device of claim 1 further comprising an interferential polarization beam splitter positioned along the path to the eye between the collimating lens and the eye for directing non-polarized light backscattered from said retina to said first position-sensitive photodetector and for directing polarized light reflected from said cornea to said second position-sensitive photodetector.

3. The measuring device of claim 2, wherein the light source producing the probing beam comprises a laser light, the laser light probing beam being directed by said interferential polarization beam splitter and separately directs non-polarized light as scattered back from the retina to said photodetector and polarized light reflected from the anterior surface of the cornea to said second photodetector.

4. The measuring device recited in claim 3, wherein, between the interferential polarization beam splitter and the eye in the path of the probing beam a group of lenses with a variable optical power is installed, forming a retina image, focused at infinity for the ametropic eye, and the photosensitive surface of the photodetector is coincident with the front focal plane of the objective lens and is located behind the interferential polarization beam splitter in the path of light scattered by the retina.

5. The measuring device recited in claim 3, further comprising an optical axis bending mirror and a plate with a gaze fixation test pattern optically coupled with the photosensitive photodetector and located between the photodetector and the objective lens and another varifocal group of lenses with a variable optical power, serving to form the test pattern image visible to the eye at a distance corresponding to a variably selected accommodation, another varifocal group of lenses is positioned between the optical axis bending mirror and the interferential polarization beam splitter and the optical axis bending mirror being mounted on a movable base making it possible to displace the mirror so as to enable the light radiation scattered by the retina to reach the photodetector during the measurement of the patients eye characteristics.

6. The measuring device recited in claim 3, wherein another optical axis bending mirror is located in the laser beam path after the last optical element, another mirror being followed by an optical calibration unit with a retina simulator whose optical characteristics are equivalent to those of the human eye retina.

7. The measuring device recited in claim 6, wherein the another optical axis bending mirror is mounted on a movable base so that it can be located in the probing laser beam path for measuring the retina standard characteristics and can be withdrawn therefrom before measuring eye aberration refraction.

8. The measuring device recited in claim 6, wherein the another optical axis bending mirror further comprises an optical coating which permits selective transmission of light such that it needs not be removed from the probing laser beam path when measuring eye aberration refraction.

9. The measuring device recited in claim 3, wherein there is an additional beam splitter leading to a channel for verifying the alignment of the device with the eye.

10. The measuring device of claim 9, wherein the channel for verifying the alignment of the device and the patients eye comprises one or more point light source and a TV or optoelectronic photodetector serving to display an image of the eye and produce a signal enabling the measurement of the ocular characteristics when the optical axis of the measuring device and the visual axis of the patients eye coincide.

11. The measuring device of claim 10, wherein the channel produces an automatic permission signal via an electronic circuitry or a computer electronically linked to said channel contains a program recognizing said automatic permission signal and directing measurement of the ocular characteristics directly upon achieving preset or derived alignment criteria according to the permission signal.

12. An instrument for measuring aberration refraction of an eye having a visual axis, the instrument comprising: a lens system defining an instrument optical axis; an alignment device for aligning the visual axis of the eye with the instrument optical axis; a light source producing a probing beam projected through the lens system parallel to the instrument optical axis and selectably positionable partially off-set from the instrument optical axis so that said probing beam imates upon the eye parallel to the instrument optical axis at a plurality of impingement locations on the cornea of the eye; a first photodetector for measuring the position of probing beam light scattered back from the retina of the eye to measure aberration refraction of the eye at plurality of locations corresponding to each of said plurality of impingement locations; a second photodetector for measuring the position of probing light beam reflected from the cornea at said plurality of impingement locations, and a computer for receiving input from said first and second photodetectors to calculate said total refraction aberration and said component thereof due to said cornea.

13. An instrument for measuring aberration refraction of an eye according to claim 12 wherein said first and said second photodetectors are selected from the group comprising: a quadrant photodetector, lateral position sensing detector, orthogonally placed linear array photodetectors, XY matrix photodetectors, or CCD detector.

14. An instrument for measuring aberration refraction of an eye as in claim 12 wherein said polarized light comprises laser light and further comprising an interferential polarization beam splitter positioned along said probing beam path for directing the probing beam polarized laser light into the eye and positioned along the visual axis of the eye between the eye and said first and said second photodetectors for permitting only non-polarized light scattered back from the retina of the eye to be detected by said first photodetector and for permitting only said polarized light reflected from said cornea to be detected by said second photodetector.

15. An instrument for measuring aberration refraction of an eye as in claim 12 further comprising: an illumination source producing a target image collimated and projected to the eye along and coincident with the instrument optical axis for fixing the gaze of the eye at a predetermined image focus distance and for aligning the visual axis of the eye coincident to said instrument axis and a varifocal telescopic lens group adjustable to regulate eye accommodation at a fixed focal distance for the target image.

16. An instrument for measuring aberration refraction of an eye as in claim 12 further comprising: a varifocal ametropia compensator including an adjustable telescopic lens system for focusing the probing beam to compensate for ametropia of the eye.

17. An instrument for measuring aberration refraction of an eye as in claim 16 further comprising: a calibration unit for calibration of the instrument to correct for lens system induced errors and to correct for errors induced by the adjustment of the varifocal telescopic lens group to compensate for eye ametropia.

18. An aberration refractometer comprising:
   a) an optical beam input channel which generates parallel light rays along an optical axis at spatially defined points onto an eye of a patient, either simultaneously or sequentially, including at least one light source and at least one lens;
   b) an eye alignment verification channel for confirming alignment of the visual axis of the eye as the patient maintains fixation with the optical axis of the input channel;
   c) a fixation target channel including at least one visual target which can be adjusted manually or in an automatic fashion to simulate different focal distances and which is in optical communication with the eye;
   d) a retinal spot position-detecting channel in optical communication with the eye including at least one first photodetector for recording at least one characteristic of a first portion of input channel light from at least one of said spatially defined points and scattered back from the retina of the eye; and
   e) a cornea reflection position detecting channel in optical communication with the eye including at least one second photodetector for recording at least one characteristic of a second portion of input channel light from said at least one of said spatially defined points and reflected back from said cornea.

19. The aberration refractometer of claim 18 further comprising a computer, electronic circuitry and a program for monitoring alignment of the visual axis of the eye and the input channel and automatically directing the generation of probing light rays upon eye alignment verification.

20. The aberration refractometer as in claim 18 further comprising computer electronic circuitry for receiving position data from said first and second photodetectors and for comparing said data for each of said plurality of impingement points for determining the total eye refraction aberration and the components due to non-homogeneity of the cornea.

21. The aberration refractometer as in claim 18 further comprising computer electronic circuitry for producing a spatially resolved map for all of said spatially defined impingement points.

22. A method for synchronous mapping of the total refraction non-homogeneity of the eye and selected refractive components of the total refraction non-homogeneity, said method comprising steps of:
   a) directing a measuring beam of light into said eye, the cross-section of beam being narrower than the entrance aperture of said eye, said beam being centered and its axis coinciding with the visual axis of said eye, said beam having a first portion thereof passing through an anterior surface of said eye to impinge upon the cornea of said eye, as well as having a second portion thereof reflecting from the corneal surface;

b) changing the position of a measuring point of beam entrance into said eye keeping said beam parallel to said visual axis;

c) measuring an offset between the location on the retina at which said beam impinges on the retina at the central position of said beam and the changed position of said measuring point;

d) determining the total refractive characteristic of said eye from the measured offset in step 22(*c*);

e) determining the angle of reflection of said second portion of said measurable beam reflected from said cornea;

f) determining the partial refractive characteristic, caused by said cornea, from the determined angle of reflection in step 22(*e*);

g) comparing, in each measuring point, the total refractive characteristic determined in step 22(*d*) with the partial refractive characteristic determined in step 22(*c*)by means of subtraction of said partial characteristic from said total refractive characteristic;

h) storing refractive characteristics determined in steps 22(*d*), 22(*f*) and 22(*g*) for each measuring point;

i) transforming the discrete sets of said refractive characteristics into continuous surfaces by means of approximation; and j) presenting said surfaces as color coded charts on the screen of a display or in any other way of presentation of the three-dimensional information.

23. The method recited in claim 22 wherein the step of determining the angle of reflection from the comer further comprises the steps of:

a) projecting the reflected part of said beam from the cornea at said measuring point onto a semitransparent light scattering screen positioned out of the zone of said entrance aperture of said eye; and b) measuring the coordinates of the location of the beam projection on said screen.

24. The method recited in claim 22 further comprising:

a) limiting a spatial zone of determining mean value of refraction of said eye to a cross-sectional area of said eye less than or equal to the cross-sectional area of said entrance aperture of said eye; and b) determining the zonal refraction by averaging the sets of values determined in steps 22(*d*), 22(*f*), or 22(*g*) for the measuring points inside said spatial zone.

25. The method recited in claim 22 further comprising:

a) comparing the refraction characteristic in each measuring point determined in steps 22(*d*), or 22(*g*) with the corresponding refraction characteristic for the neighbor measuring point by means of extracting the value of the refractive characteristic in said measuring point from the value of the refractive characteristic in the measuring point neighbor to said measuring point;

b) inserting an additional measuring point, located between the neighboring measuring points used for the comparison in step 25(*a*), if the difference value determined in step 25(*a*) is higher than a specified threshold; and c) repeating the steps 22(*a*)–22(*k*) until there is no more value determined in step 25(*a*) higher than said specified threshold.

26. A device for synchronous mapping of the total refraction non-homogeneity of the eye and its refractive components comprising:

a) means for providing a narrow beam of light to be directed into said eye;

b) means for shifting said beam over the entrance aperture of said eye in parallel to itself and positioning said beam in a measuring point;

c) means for detecting the light back-scattered from the retina of said eye;

d) means for measuring an offset between the location on the retina at which said beam impinges on said retina for the first position when the beam's axis coincides with the visual axis of said eye and for the second position when the beam is displaced to said measuring point;

e) means for calculating the total refractive characteristic of said eye in said measuring point from the measured offset by means of 26(*d*);

f) a semitransparent light-scattering screen inserted in outer zone of said entrance aperture;

g) means for detecting the light reflected from the cornea of said eye and projected on said semitransparent light-scattering screen;

h) means for measuring the coordinates of the location of said beam reflected from said cornea in said measuring point and projected on said screen;

i) means for calculating the partial refraction characteristic of said eye in said measuring point, caused by said cornea, from the coordinates measured by means of 26(*h*);

j) means for calculating the difference between the values of said total refractive characteristic calculated by means of 26(*d*) and the value of said partial refractive characteristic caused by said cornea and calculated by means of 26(*i*);

k) means for storing refractive characteristics calculated by means of 26(*d*), 26(*i*), and 26(*j*) for each measuring point;

l) means for transforming the discrete sets of said refractive characteristics into continues three-dimensional distributions of said refractive characteristics; and m) means for displaying said three-dimensional distributions of said refractive characteristics.

27. The device recited in claim 26 comprising means for calculating the averaged values of refraction within a spatially limited zone of the entrance aperture of said eye, said zone being smaller or equal to said entrance aperture of said eye.

28. The device recited in claim 26 comprising:

a) means for calculating the absolute difference between the values of the same refractive characteristic in each pair of neighboring measuring points; and b) means for producing a control command for repeating the measurements of said refractive characteristic in an additional measuring point inserted between said neighboring points.

29. The device recited in claim 26 comprising said screen having the shape of the figure of rotation of straight or curved line about the optical axis of said beam in the central position of said beam.

30. A device for measuring aberration refraction of both of a patient's eyes, comprising: a polarized light source producing a probing beam along paths of a patient's eyes; a telescopic system of lenses having an entrance pupil and an exit pupil; a two-coordinate deflector consisting of two single-coordinate deflectors separated by a zone; a deflection control unit; an aperture stop; a field stop; a collimating lens; a first position-sensitive photodetector with an objective lens operatively positioned for receiving non-polarized light reflected from the retina of both eyes, one eye at a time, a second position-sensitive photodetector for simultaneously and selectively receiving polarized light reflected from the cornea of both eyes, one eye at a time, coordinated to receive polarized light from the cornea of the same eye as the non-polarized light is received from the retina; and a data processing and display unit including a computer coupled to said first and second photodetectors for calculating total eye refraction aberration and the component caused by cornea aberration separately and substantially simultaneously for both of the patient's eyes.

* * * * *